(12) United States Patent
Li et al.

(10) Patent No.: US 12,098,414 B2
(45) Date of Patent: Sep. 24, 2024

(54) MONITORING REACTOR AND METHOD FOR USING THE SAME

(71) Applicant: Nankai University, Tianjin (CN)

(72) Inventors: Tian Li, Tianjin (CN); Qixing Zhou, Tianjin (CN)

(73) Assignee: Nankai University, Tianjin (CN)

( * ) Notice: Subject to any disclaimer, the term of this patent is extended or adjusted under 35 U.S.C. 154(b) by 727 days.

(21) Appl. No.: 17/217,041

(22) Filed: Mar. 30, 2021

(65) Prior Publication Data

US 2022/0220526 A1 Jul. 14, 2022

(30) Foreign Application Priority Data

Jan. 8, 2021 (CN) .......................... 202110022998.5

(51) Int. Cl.
*C12Q 1/02* (2006.01)
*B09C 1/10* (2006.01)
*G01N 27/327* (2006.01)
*G01N 33/24* (2006.01)

(52) U.S. Cl.
CPC ................. *C12Q 1/02* (2013.01); *B09C 1/10* (2013.01); *G01N 27/327* (2013.01); *G01N 33/24* (2013.01)

(58) Field of Classification Search
CPC .... C12Q 1/02; G01N 27/327; G01N 27/3277; G01N 33/24; B09C 1/085; H01M 8/16; H01M 2250/10
See application file for complete search history.

(56) References Cited

U.S. PATENT DOCUMENTS

2015/0352609 A1* 12/2015 Zuo .................. B09C 1/085
205/766
2020/0271616 A1* 8/2020 Jin .................. G01N 27/286

* cited by examiner

*Primary Examiner* — C. Sun
(74) *Attorney, Agent, or Firm* — Dorsey & Whitney LLP

(57) ABSTRACT

It is provided a monitoring reactor and a method for using the same, belonging to microbiologic electrochemical early-warning technology. The monitoring reactor enriches microorganisms therein before use, and consumes the organic matter. When the organic matter in the monitoring reactor is consumed completely, i.e. the microorganisms are in a starved state, the monitoring reactor is placed in a system to be monitored for monitoring, thereby avoiding the interference of the organic matter in the soil in the monitoring reactor to the electrical signal and improving the monitoring accuracy. Furthermore, since the electrical signal in the monitoring reactor is conducted through the electricigens, the process of generating electricity of the electricigens is a process of growth and propagation of microorganism. This process is less affected by the monitored environment. Therefore, the signal output process is stable, without swell and sag of the electrical signal.

20 Claims, 5 Drawing Sheets

MONITORING REACTOR AND METHOD FOR USING THE SAME

CROSS REFERENCE TO RELATED APPLICATION

This application claims priority to Chinese Patent Application No. 202110022998.5, entitled "Monitoring Reactor and Method for Using the Same" filed with the Chinese Patent Office on Jan. 8, 2021, which is incorporated herein by reference in its entirety.

TECHNICAL FIELD

The present disclosure relates to the field of microbial electrochemical early-warning technology, and in particular, to a monitoring reactor and a method for using the same.

BACKGROUND ART

The exploration and utilization of oilfield greatly improves the economic level of a country. However, it also brings severe petroleum pollution problems during exploration and transportation. Law of the People's Republic of China on the Prevention and Control of Soil Pollution published in 2018, also places higher requirements on high efficient and environment friendly remediation of petroleum polluted soil. With increasing knowledge of ecological damage and health risk caused by petroleum pollution in various countries of the world, monitoring of leaked petroleum hydrocarbons in time and quickly can greatly reduce workload of remediation, thereby alleviating soil pollution.

At present, monitoring breathing process of microorganisms is the most common method for characterizing health degree of soil, and the method achieves health monitoring of soil by reflecting the biological activity of soil and the content of organic matter in soil. However, this method is material-consuming and time-consuming. Furthermore, this method has a high requirement on water content of soil environment, and has a low sensitivity to water saturated soil or soil with low water permeability.

The microbiological electrochemical technology evaluates level of microbiological activity of soil by quantifying electrons released during microorganisms degrading the organic matter in soil, and thus implements evaluating and monitoring of the health degree of soil by means of voltage variation. This technology has advantages such as real-time, low cost and low consumption. In recent years, the microbiological electrochemical technology has achieved efficient degradation of petroleum hydrocarbon molecules in soil; however, it lacks a technology that can be operated stably and can monitor the health degree of soil polluted by petroleum hydrocarbon.

SUMMARY

In view of the above, an object of some embodiments is to provide a monitoring reactor and a method for using the same. The monitoring reactor provided by the present disclosure can perform a real-time, accurate and stable monitoring of degradation process of petroleum hydrocarbon contaminants.

In order to achieve the above object of the embodiments, the present disclosure provides the following technical solutions:

The present disclosure provides a monitoring reactor, including: an outside wrapping steel mesh 4, having a shape of a hollow inverted cone frustum with a top opened; a biochar structure 2, located inside the outside wrapping steel mesh, the biochar structure having a shape of a hollow inverted cone frustum with a top opened; a hollow cylindrical steel mesh structure 3, located inside the biochar structure. The outside wrapping steel mesh 4, the biochar structure 2 and the hollow cylindrical steel mesh structure 3 are coaxial. A mixture of cross-linked sodium polyacrylate and soil particles is filled between the outside wrapping steel mesh 4 and the biochar structure 2, and between the biochar structure 2 and the hollow cylindrical steel mesh structure 3. The soil particles are farmland soil particles. The biochar structure is an anode and the hollow cylindrical steel mesh structure is a counter electrode. The biochar structure and the hollow cylindrical steel mesh structure are respectively connected to an external wireless-internet-supplying power collector 1 via wires. The water absorption effect of the cross-linked sodium polyacrylate in the monitoring reactor provided by the present disclosure can cause the water body of the organic contaminants in soil to flow, so as to output an electrical signal from a microbiological film at the anode, thereby achieving a monitoring purpose. The monitoring reactor of the present disclosure enriches the microorganisms therein before use, and consumes the organic matter. When the organic matter in the monitoring reactor is consumed completely, i.e. the microorganisms are in a starved state, the monitoring reactor is placed into a system to be detected for detection, thereby avoiding interference of the organic matter in the soil in the monitoring reactor to the electrical signal and improving monitoring accuracy. Furthermore, since the electrical signal in the monitoring reactor is conducted through the electricigens, a process of generating electricity of the electricigens is a process of growth and propagation of microorganisms. This process is less affected by the monitored environment, and thus, the signal output process is stable, the swells and sags events of the electrical signal do not occur. Furthermore, the monitoring reactor of the present disclosure is plug-and-play and convenient to use. The monitoring reactor can not only implement a technical diagnosis on the soil with a potential risk of being polluted, but also monitor unpolluted soil in real time, and thus can be used widely.

Furthermore, the monitoring reactor provided by the present disclosure is pretreated before use. An external source voltage is applied between the biochar structure and the hollow cylindrical steel mesh structure. When an electrical signal is lower than 0.01 mA, the pretreatment can enrich the microorganisms in the soil particles by utilizing a small amount of organic carbon source in the soil particles to provide a microbiological basis for subsequent monitoring.

Figure 1:
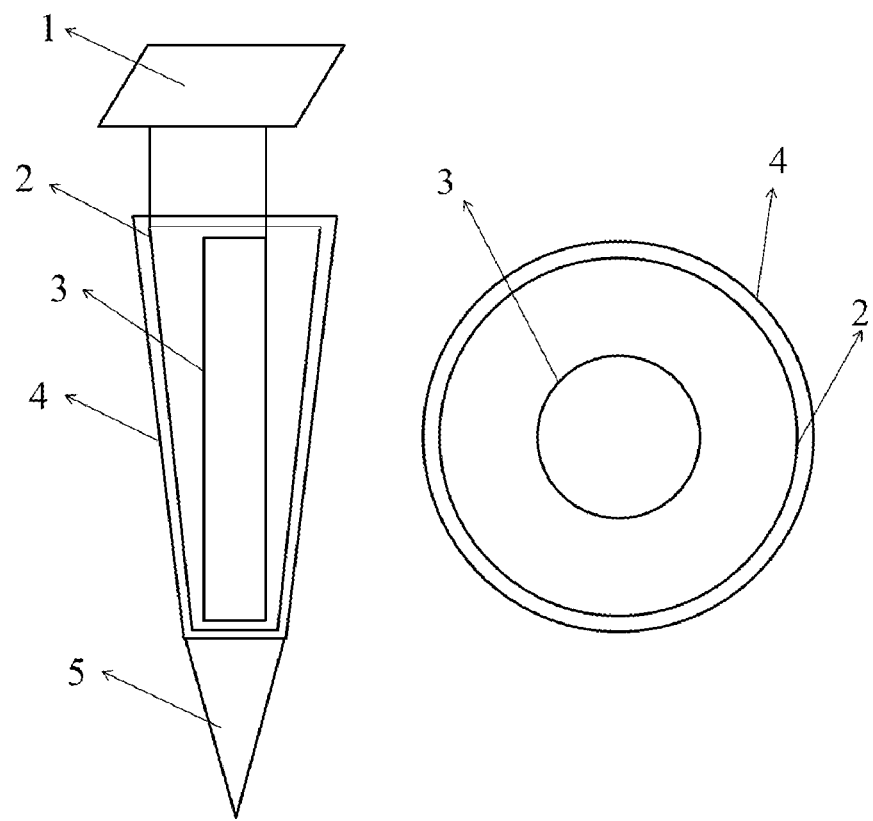
FIG. 1 is a schematic structural diagram of a monitoring reactor according to the present disclosure, on the right of which showing a cross-sectional diagram of the monitoring reactor.

List of reference numerals: 1 wireless-internet-supplying power collector; 2 biochar structure; 3 hollow cylindrical steel mesh structure; 4 outside wrapping steel mesh; and 5 soil exploitation cone.

DETAILED DESCRIPTION OF THE EMBODIMENTS

FIG. 1 is a schematic structural diagram of a monitoring reactor provided by the present disclosure, on the right of which showing a cross-sectional diagram of the monitoring reactor. Furthermore, a reference number 1 indicates a wireless-internet-supplying power collector; a reference number 2 indicates biochar structure; a reference number 3 indicates a hollow cylindrical steel mesh structure; a reference number 4 indicates an outside wrapping steel mesh; and a reference number 5 indicates a soil exploitation cone. The structure of the monitoring reactor provided by the present disclosure will be described in detail in combination with FIG. 1

It is provided a monitoring reactor by the present disclosure, including an outside wrapping steel mesh 4, a biochar structure 2 and a hollow cylindrical steel mesh structure 3.

The monitoring reactor provided by the present disclosure includes an outside wrapping steel mesh 4, and the outside wrapping steel mesh 4 has a shape of a hollow inverted cone frustum with a top opened. The thickness of the outside wrapping steel mesh is preferably within a range of 0.4-0.6 cm, and further preferably 0.5 cm. In the present disclosure, an aperture of the outside wrapping steel mesh is preferably within a range of 10-20 mesh, and further preferably 10 mesh. In the present disclosure, the outside wrapping steel mesh is configured to separate a sample to be monitored from the monitoring reactor. In a specific embodiment of the present disclosure, the size of the outside wrapping steel mesh preferably includes: an upper radius within a range of 5-6 cm, preferably of 5.2 cm; a lower radius within a range of 2-3 cm, preferably of 2.5 cm; and a height within a range of 15-20 cm, preferably of 16 cm.

The monitoring reactor provided by the present disclosure includes the biochar structure 2 located inside the outside wrapping steel mesh 4. The biochar structure 2 has a shape of a hollow inverted cone frustum with a top opened. The thickness of the biochar structure is preferably within a range of 1.5-2.5 cm, and further preferably 2 cm. In a specific embodiment of the present disclosure, the size of the biochar structure preferably includes: an upper radius within a range of 4.8-5.8 cm, preferably of 5 cm; a lower radius within a range of 1.7-2.7 cm, preferably of 2.2 cm; and a height within a range of 13-18 cm, preferably of 15 cm.

The monitoring reactor provided by the present disclosure includes the hollow cylindrical steel mesh structure 3 located inside the biochar structure 2. The hollow cylindrical steel mesh structure is formed by winding a steel mesh into a cylindrical shape. In the present disclosure, a thickness of the hollow cylindrical steel mesh structure is preferably 0.2 cm. An aperture of the hollow cylindrical steel mesh structure 3 preferably is within a range of 10-20 mesh, and further preferably 10 mesh. In a specific embodiment of the present disclosure, a size of the hollow cylindrical steel mesh structure preferably includes: a radius within a range of 1.5-2.5 cm, further preferably of 2 cm; and a height within a range of 13-18 cm, and more preferably of 14 cm.

In the present disclosure, the outside wrapping steel mesh, the biochar structure and the hollow cylindrical steel mesh structure are coaxial.

In the present disclosure, a mixture of cross-linked sodium polyacrylate and soil particles is filled between the outside wrapping steel mesh and the biochar structure, and between the biochar structure and the hollow cylindrical steel mesh structure. A mass ratio of the cross-linked sodium polyacrylate to the soil particles is within a range of 1:1-1:5, particularly preferably 1:1, 1:2.5 or 1:5. In a specific embodiment of the present disclosure, when the size of the outside wrapping steel mesh includes the upper radius of 5.2 cm, the lower radius of 2.5 cm, and the height of 16 cm; the size of the biochar structure includes the upper radius of 5 cm, the lower radius of 2.2 cm, and the height of 15 cm; and the size of the hollow cylindrical steel mesh structure includes the radius of 2 cm and the height of 14 cm, mass of the mixtures of cross-linked sodium polyacrylate and soil particles filled between the outside wrapping steel mesh and the biochar structure, and between the biochar structure and the hollow cylindrical steel mesh structure is preferably within a range of 60-90 g, and further preferably 80 g. In the present disclosure, the soil particles are farmland soil particles. Preferably, the farmland soil particles are pretreated to be as the soil particles. The pretreatment method is preferably removing impurities and smashing. The present disclosure does not limit the manner of removing impurities and smashing, as long as the impurities can be removed completely and the soil does not leak out of the monitoring reactor. In the present disclosure, the addition of the mixture of cross-linked sodium polyacrylate and soil particles can maintain local environmental stability and provide a small amount of carbon source.

In the present disclosure, the biochar structure is an anode and a hollow cylindrical steel mesh structure is a counter electrode. The biochar structure and the hollow cylindrical steel mesh structure are respectively connected to an external wireless-internet-supplying power collector 1.

In the present disclosure, the monitoring reactor is used, preferably with the cooperation of the soil exploitation cone 5. The size of the soil exploitation cone 5 is not specifically limited in the present disclosure, as long as the soil exploitation cone 5 can be matched with the monitoring reactor. In the present disclosure, the soil exploitation cone enables the monitoring reactor to enter a system to be detected, more quickly and nondestructively.

It is further provided a method for using the monitoring reactor according to the above technical solution, including the following steps of:

applying an external source voltage between the biochar structure and the hollow cylindrical steel mesh structure of the monitoring reactor; inserting the monitoring reactor into a degradation system when the electrical signal is lower than 0.01 mA; and monitoring degradation of contaminants.

In the present disclosure, the external source voltage is preferably within a range of 0.2-0.7 V.

In the present disclosure, the application of the external source voltage can achieve enrichment of microorganisms by utilizing microorganisms and a small amount of organic matter in the soil particles. When the electrical signal becomes a maximum, it indicates that the microorganisms are completely enriched. When the electrical potential is continued to be supplied until the electrical signal is below 0.01 mA, it indicates that the organic matter in the soil particles in the monitoring reactor is completely consumed, and the microorganisms at this time are in a starved state. At this time, the monitoring reactor is placed in a system to be monitored, and the microorganisms in the monitoring reactor will grow by utilizing the microorganisms in the system to be monitored and then generate an electrical signal. The generated electrical signal can directly reflect a content of organic matter in the monitored system, thereby achieving monitoring of the content of organic matter in the monitored system.

Figure 2:
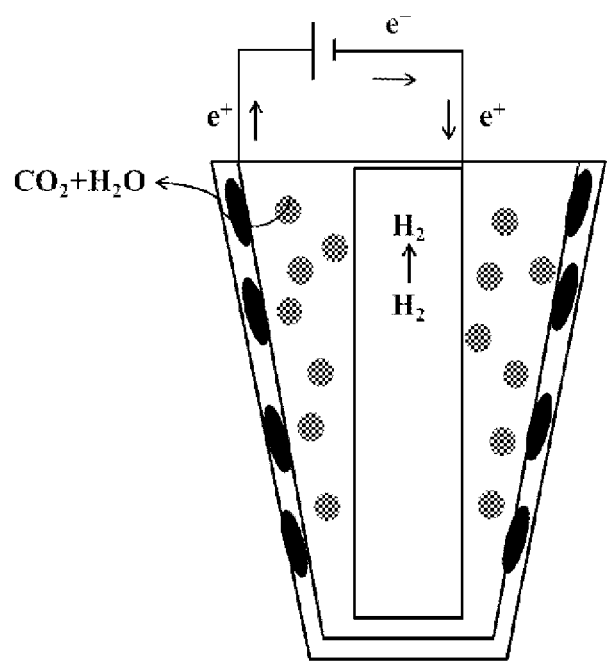
FIG. 2 is a schematic diagram of dynamically monitoring petroleum hydrocarbons by the monitoring reactor according to the present disclosure.

FIG. 2 is a schematic diagram of dynamically monitoring petroleum hydrocarbons by a monitoring reactor provided by the present disclosure.

A monitoring reactor and a method for using the monitoring reactor provided by the present disclosure are described in detail below with reference to the embodiments, but they cannot be construed as limiting the scope of protection of the present disclosure.

EXAMPLE 1

A monitoring reactor is constructed. Specifically, an outside wrapping steel mesh with an aperture of 10 mesh and a thickness of 0.5 cm and having an upper radius of 5.2 cm, a lower radius of 2.5 cm and a height of 16 cm is firstly designed to protect stability of the monitoring reactor in soil. Then, the biochar structure with a thickness of 2.0 cm and having an upper radius of 5 cm, a lower radius of 2.2 cm and a height of 15 cm is placed inside the outside wrapping steel mesh. A titanium wire is embedded as an electron collecting wire into the biochar structure. Finally, a hollow cylindrical steel mesh structure with an aperture of 10 mesh, i.e. 0.2 cm and having a radius of 2 cm and a height of 14 cm is placed at a center of the biochar structure, and the hollow cylindrical steel mesh structure is used as a counter electrode. A mixture of cross-linked sodium polyacrylate and soil particles is placed between the outside wrapping steel mesh and the biochar structure, and between the biochar structure and the hollow cylindrical steel mesh structure. The mass ratio of the cross-linked sodium polyacrylate to the soil particles in the mixture is 1:1.

Figure 3:
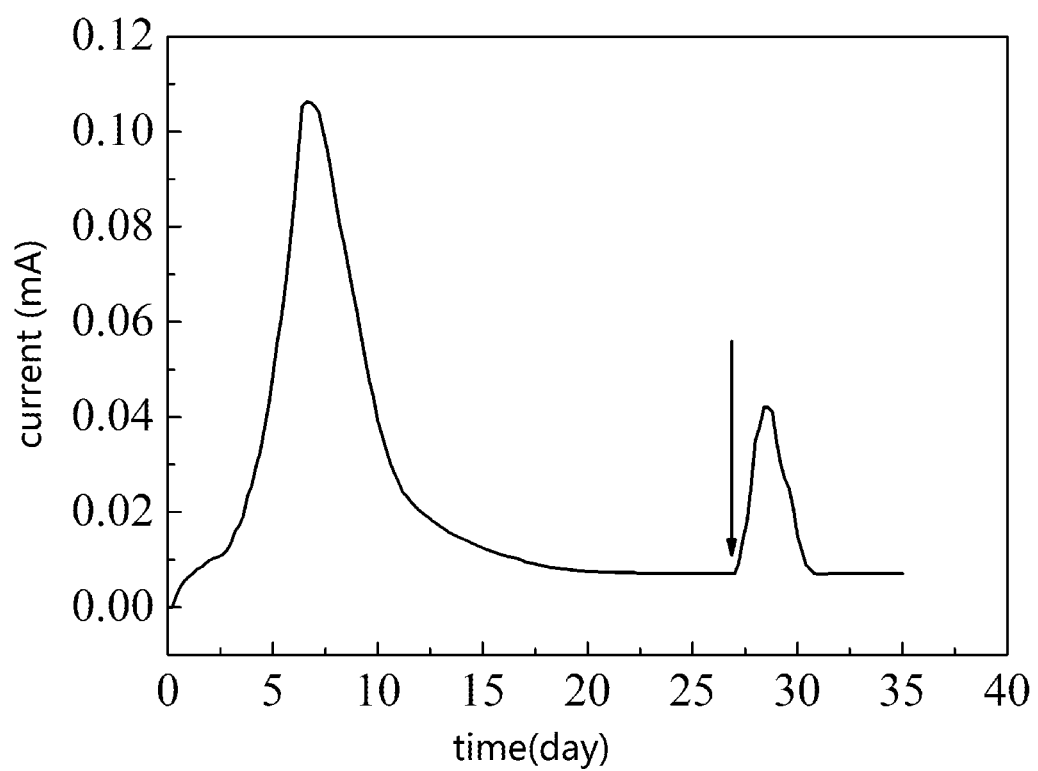
FIG. 3 is a graph of current changes when dynamically monitoring clean soil by the monitoring reactor in Embodiment 1.

A 0.2 V direct current supply voltage is applied between the biochar structure and the hollow cylindrical steel mesh structure to form a potential difference therebetween to ensure normal flow of electrons. Thus, an electrical signal is generated and a pretreatment i.e., enrichment of the electro-active microorganisms on the anode is completed. The carbon source during enrichment of the electro-active microorganisms comes from a small amount of organic matter in the soil environment. The current data is shown in FIG. 3, where, in front of the arrow, it shows a change in the electrical signal generated during enriching microorganisms and consuming a small amount of organic matter in the soil. When the electrical signal reaches the maximum, it indicates that the microorganisms are enriched completely. Then the electric potential is continued to be supplied, and when the electrical signal is lower than 0.01 mA, the pretreatment is completed.

The pretreated monitoring reactor is inserted into the polluted soil containing 0 mg/kg petroleum hydrocarbon. A content of petroleum hydrocarbon molecules in the soil is indicated by fluctuated changes of the electrical signal. As the change of the electrical signal shown behind the arrow in FIG. 3, it indicates that when the petroleum hydrocarbon concentration in the soil is 0 mg/kg, the microorganisms can only decompose some organic matter in the soil. The oxidation-reduction reaction generates very few electrons, and after a small peak (0.04 mA), the current quickly falls back to a starved state and is maintained below 0.01 mA. The highest current peak generated in the clean soil is lower than the current peak generated in the pretreatment process, mainly due to an accelerated consummation of organic matter by the accumulated microorganisms on the biological film.

EXAMPLE 2

Figure 4:
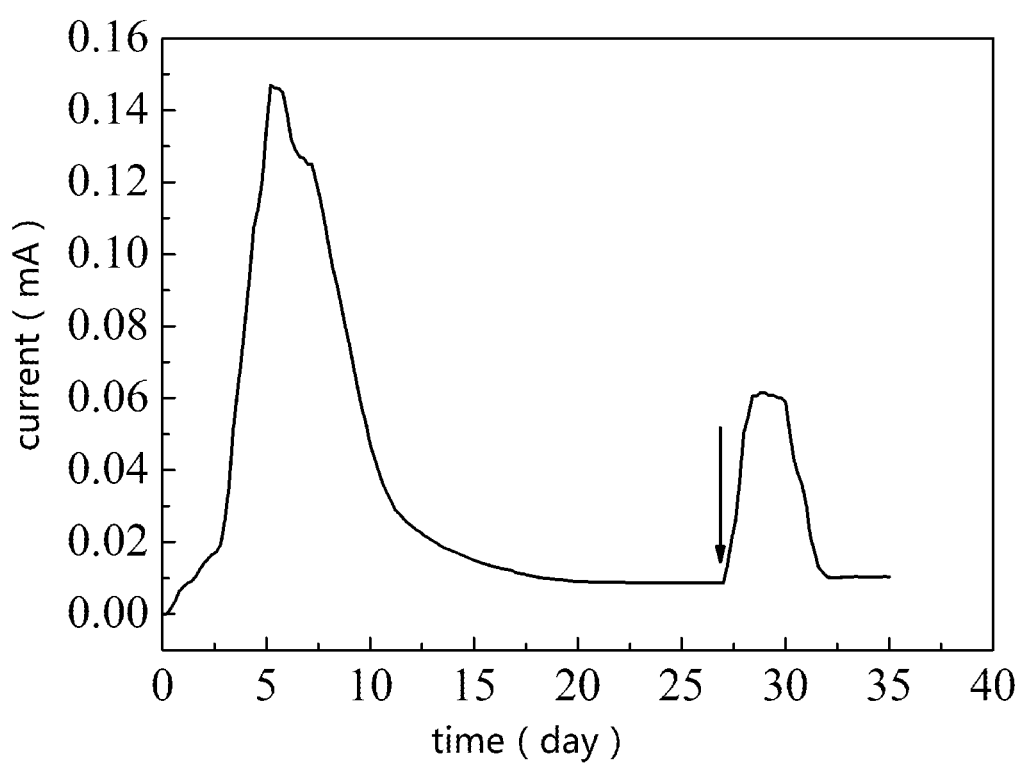
FIG. 4 is a graph of current changes when dynamically monitoring the soil containing 50 mg/kg petroleum hydrocarbon by the monitoring reactor in Embodiment 2.

A monitoring reactor is constructed. The difference from Example 1 is that the mass ratio of cross-linked sodium polyacrylate to soil particles is 1:2.5, and that a 0.5 V direct current supply voltage is applied between the biochar structure and the hollow cylindrical steel mesh structure. The obtained current data is shown in FIG. 4, where in front of the arrow, it indicates a change of the electrical signal generated during enriching microorganisms and consuming a small amount of organic matter in the soil. When the electrical signal reaches the maximum, it indicates that the microorganisms are enriched completely. The electric potential is continued to be supplied, and when the electrical signal is lower than 0.01 mA, the pretreatment is completed.

The pretreated monitoring reactor is inserted into the polluted soil containing 50 mg/kg petroleum hydrocarbon. A content of petroleum hydrocarbon molecules in the soil is indicated by fluctuated change of the electrical signal. As a change of the electrical signal shown behind the arrow in FIG. 4, it indicates that when the petroleum hydrocarbon concentration in the soil is 50 mg/kg, the microorganisms can decompose petroleum hydrocarbon to generate a portion of organic matter for powering the electro-active microorganisms for oxidative reduction process to produce electrons. The current gradually recovers in a short time and reaches a maximum current of 0.06 mA, the maximum current is maintained for 24 hours or more.

Embodiment 3

Figure 5:
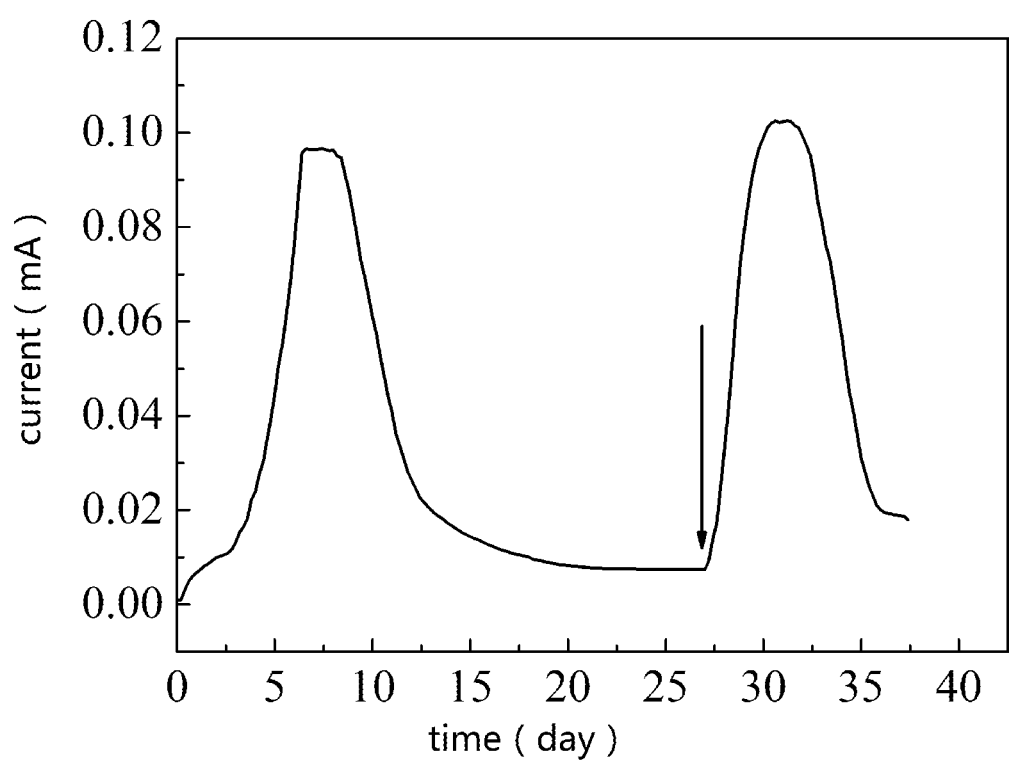
FIG. 5 is a graph of current changes when dynamically monitoring the soil containing 200 mg/kg petroleum hydrocarbon by the monitoring reactor in Embodiment 3.

A monitoring reactor is constructed. The difference from Example 1 is that the mass ratio of cross-linked sodium polyacrylate to soil particles is 1:5; and a 0.7V direct current supply voltage is applied between the biochar structure and the hollow cylindrical steel mesh structure. The obtained current data is as shown in FIG. 5, where in front of the arrow, it indicates a change of the electrical signal generated during enriching microorganisms and consuming a small amount of organic matter in the soil. When the electrical signal reaches a maximum, it indicates that the microorganisms are enriched completely. The electric potential is continued to be supplied, and when the electrical signal is lower than 0.01 mA, the pretreatment is completed.

The pretreated monitoring reactor is inserted into the polluted soil containing 200 mg/kg petroleum hydrocarbon. A content of petroleum hydrocarbon molecules in the soil is indicated by fluctuated change of the electrical signal. As a change of the electrical signal shown behind the arrow in FIG. 5, it indicates that when the petroleum hydrocarbon concentration in the soil is 200 mg/kg, the microorganisms can decompose petroleum hydrocarbon to generate a portion of organic matter for powering the electro-active microorganisms for oxidative reduction process to produce electrons. The current gradually recovers in a short time and reaches a maximum current of 0.10 mA, the maximum current is maintained for 24 hours or more.

The above description is merely a preferred embodiment of the present disclosure, and it should be pointed out that, for an ordinary person skilled in the art, several improvements and modifications can be made without departing from the principle of the present disclosure, and these improvements and modifications should also be regarded as the scope of protection of the present disclosure.

What is claimed is:

1. A monitoring reactor, comprising:
   an outside wrapping steel mesh, having a shape of a hollow inverted cone frustum with a top opened;
   a biochar structure, located inside the outside wrapping steel mesh, the biochar structure having a shape of a hollow inverted cone frustum with a top opened;
   a hollow cylindrical steel mesh structure, located inside the biochar structure,
   wherein the outside wrapping steel mesh, the biochar structure and the hollow cylindrical steel mesh structure are coaxial;
   a mixture of cross-linked sodium polyacrylate and soil particles is filled between the outside wrapping steel mesh and the biochar structure, and between the biochar structure and the hollow cylindrical steel mesh structure; the soil particles are farmland soil particles;
   wherein the biochar structure is an anode and the hollow cylindrical steel mesh structure is a counter electrode;
   wherein the biochar structure and the hollow cylindrical steel mesh structure are respectively connected to an external wireless-internet-supplying power collector via wires.

2. The monitoring reactor according to claim 1, wherein apertures of the outside wrapping steel mesh and of the hollow cylindrical steel mesh structure are both within a range of 10-20 mesh.

3. The monitoring reactor according to claim 1, wherein a thickness of the biochar structure is within a range of 1.5-2.5 cm.

4. The monitoring reactor according to claim 1, wherein the outside wrapping steel mesh has an upper radius within a range of 5-6 cm, a lower radius within a range of 2-3 cm and a height within a range of 15-20 cm;
   the biochar structure has an upper radius within a range of 4.8-5.8 cm, a lower radius within a range of 1.7-2.7 cm and a height within a range of 14-19 cm;
   the hollow cylindrical steel mesh structure has a radius within a range of 1.5-2.5 cm and a height within a range of 13-18 cm.

5. The monitoring reactor according to claim 2, wherein the outside wrapping steel mesh has an upper radius within a range of 5-6 cm, a lower radius within a range of 2-3 cm and a height within a range of 15-20 cm;
   the biochar structure has an upper radius within a range of 4.8-5.8 cm, a lower radius within a range of 1.7-2.7 cm and a height within a range of 14-19 cm;
   the hollow cylindrical steel mesh structure has a radius within a range of 1.5-2.5 cm and a height within a range of 13-18 cm.

6. The monitoring reactor according to claim 3, wherein the outside wrapping steel mesh has an upper radius within a range of 5-6 cm, a lower radius within a range of 2-3 cm and a height within a range of 15-20 cm;
   the biochar structure has an upper radius within a range of 4.8-5.8 cm, a lower radius within a range of 1.7-2.7 cm and a height within a range of 14-19 cm;
   the hollow cylindrical steel mesh structure has a radius within a range of 1.5-2.5 cm and a height within a range of 13-18 cm.

7. The monitoring reactor according to claim 4, wherein mass of the mixture of cross-linked sodium polyacrylate and soil particles filled between the outside wrapping steel mesh and the biochar structure, and the mixture between the biochar structure and the hollow cylindrical steel mesh structure is within a range of 60-90 g.

8. The monitoring reactor according to claim 5, wherein mass of the mixture of cross-linked sodium polyacrylate and soil particles filled between the outside wrapping steel mesh and the biochar structure, and the mixture between the biochar structure and the hollow cylindrical steel mesh structure is within a range of 60-90 g.

9. The monitoring reactor according to claim 6, wherein mass of the mixture of cross-linked sodium polyacrylate and soil particles filled between the outside wrapping steel mesh and the biochar structure, and the mixture between the biochar structure and the hollow cylindrical steel mesh structure is within a range of 60-90 g.

10. The monitoring reactor according to claim 1, wherein a mass ratio of cross-linked sodium polyacrylate to soil particles is within a range of 1:1-1:5.

11. The monitoring reactor according to claim 7, wherein a mass ratio of cross-linked sodium polyacrylate to soil particles is within a range of 1:1-1:5.

12. The monitoring reactor according to claim 8, wherein a mass ratio of cross-linked sodium polyacrylate to soil particles is within a range of 1:1-1:5.

13. The monitoring reactor according to claim 9, wherein a mass ratio of cross-linked sodium polyacrylate to soil particles is within a range of 1:1-1:5.

14. The monitoring reactor according to claim 1, wherein the monitoring reactor is provided with a soil exploitation cone when used.

15. A method for using a monitoring reactor, which includes an outside wrapping steel mesh, having a shape of a hollow inverted cone frustum with a top opened;
   a biochar structure, located inside the outside wrapping steel mesh, the biochar structure having a shape of a hollow inverted cone frustum with a top opened;
   a hollow cylindrical steel mesh structure, located inside the biochar structure,
   wherein the outside wrapping steel mesh, the biochar structure and the hollow cylindrical steel mesh structure are coaxial;
   a mixture of cross-linked sodium polyacrylate and soil particles is filled between the outside wrapping steel mesh and the biochar structure, and between the biochar structure and the hollow cylindrical steel mesh structure; the soil particles are farmland soil particles;
   wherein the biochar structure is an anode and the hollow cylindrical steel mesh structure is a counter electrode;
   the biochar structure and the hollow cylindrical steel mesh structure are respectively connected to an external wireless-internet-supplying power collector via wires;
   the method comprising:
   applying an external source voltage between the biochar structure and the hollow cylindrical steel mesh structure of the monitoring reactor;
   inserting the monitoring reactor into a degradation system when the electrical signal is lower than 0.01 mA; and
   monitoring degradation of contaminants.

16. The method according to claim 15, wherein the external source voltage is within a range of 0.2-0.7 V.

17. The method according to claim 15, wherein apertures of the outside wrapping steel mesh and of the hollow cylindrical steel mesh structure are both within a range of 10-20 mesh.

18. The method according to claim 15, wherein a thickness of the biochar structure is within a range of 1.5-2.5 cm.

19. The method according to claim 15, wherein the outside wrapping steel mesh has an upper radius within a range of 5-6 cm, a lower radius within a range of 2-3 cm and a height within a range of 15-20 cm;

the biochar structure has an upper radius within a range of 4.8-5.8 cm, a lower radius within a range of 1.7-2.7 cm and a height within a range of 14-19 cm;

the hollow cylindrical steel mesh structure has a radius within a range of 1.5-2.5 cm and a height within a range of 13-18 cm.

20. The method according to claim 17, wherein the outside wrapping steel mesh has an upper radius within a range of 5-6 cm, a lower radius within a range of 2-3 cm and a height within a range of 15-20 cm;

the biochar structure has an upper radius within a range of 4.8-5.8 cm, a lower radius within a range of 1.7-2.7 cm and a height within a range of 14-19 cm;

the hollow cylindrical steel mesh structure has a radius within a range of 1.5-2.5 cm and a height within a range of 13-18 cm.

\* \* \* \* \*